(12) United States Patent
Komar et al.

(10) Patent No.: US 10,319,464 B2
(45) Date of Patent: Jun. 11, 2019

(54) METHOD AND APPARATUS FOR IDENTIFYING TANDEM REPEATS IN A NUCLEOTIDE SEQUENCE

(71) Applicant: Seven Bridges Genomics, Inc., Cambridge, MA (US)

(72) Inventors: Peter Komar, Boston, MA (US); Yilong Li, Cambridge, MA (US)

(73) Assignee: Seven Bridges Genomics, Inc., Charlestown, MA (US)

( * ) Notice: Subject to any disclaimer, the term of this patent is extended or adjusted under 35 U.S.C. 154(b) by 308 days.

(21) Appl. No.: 15/196,085

(22) Filed: Jun. 29, 2016

(65) Prior Publication Data
US 2018/0004891 A1    Jan. 4, 2018

(51) Int. Cl.
*G01N 31/00* (2006.01)
*G16B 30/00* (2019.01)

(52) U.S. Cl.
CPC .................................. *G16B 30/00* (2019.02)

(58) Field of Classification Search
CPC ........................................................ G06F 19/22
USPC .......................................................... 702/29
See application file for complete search history.

(56) References Cited

U.S. PATENT DOCUMENTS

| | | | | |
|---|---|---|---|---|
| 6,373,971 B1 * | 4/2002 | Floratos | ................... | G06K 9/62 382/129 |
| 8,296,075 B2 * | 10/2012 | Den Hartog | ............ | G06F 19/22 700/1 |
| 2009/0117542 A1 * | 5/2009 | Maybruck | ............ | C12Q 1/6876 435/6.11 |
| 2013/0130246 A1 * | 5/2013 | Bensimon | ............ | C12Q 1/6816 435/6.11 |
| 2015/0032385 A1 * | 1/2015 | Young | ..................... | G06F 19/22 702/20 |

OTHER PUBLICATIONS

Gary Benson, 1998, Tandem repeats finder: a program to analyze DNA sequences, Nucleic Acids Research, 27:2 573-580.
Gelfand et al., 2007, TRDB—The Tandem Repeats Database, Nucleic Acids Research, 35(Suppl. 1), 80-87.

(Continued)

*Primary Examiner* — Toan M Le
*Assistant Examiner* — Xiuqin Sun
(74) *Attorney, Agent, or Firm* — Kip L. Bodi

(57) ABSTRACT

A method and corresponding apparatus for identifying tandem repeats in a nucleotide sequence is described. Tandem repeats can be identified by identifying one or more lines present in a self-alignment plot of the nucleotide sequence. The disclosed method includes identifying one or more square-shaped subregions (SSS) representing a tandem repeat and each associated with a plurality of identified candidate alignments by: i) estimating a defining point of an individual square for each of the candidate alignments, each candidate alignment having a start point and an end point, the start point and the end point positioned along adjacent sides of the individual square; ii) selecting one or more seed alignments from the one or more candidate alignments; and iii) associating the one or more candidate alignments with the one or more seed alignments. Based on the associating, a final SSS representing a tandem repeat is determined and its presence is reported.

20 Claims, 12 Drawing Sheets

Specification includes a Sequence Listing.

(56) References Cited

OTHER PUBLICATIONS

Lim et al., 2013, Review of tandem repeat search tools: A systematic approach to evaluating algorithmic performance, Briefings in Bioinformatics, 14(1), 67-81.
Noe et al., 2005, YASS: enhancing the sensitivity of DNA similarity search, Nucleic Acids Research 33:W540-W543.

* cited by examiner

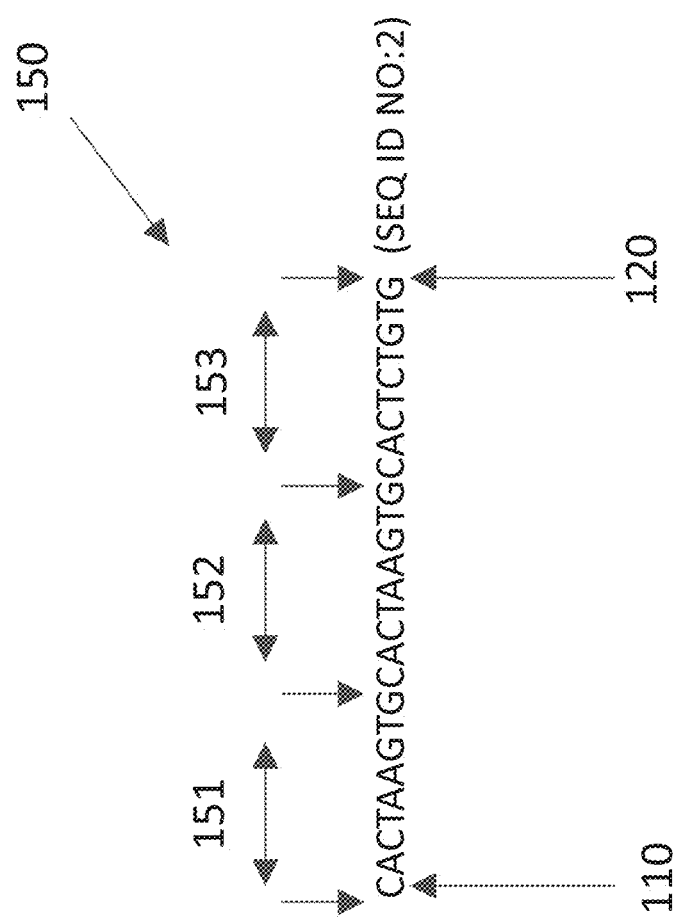

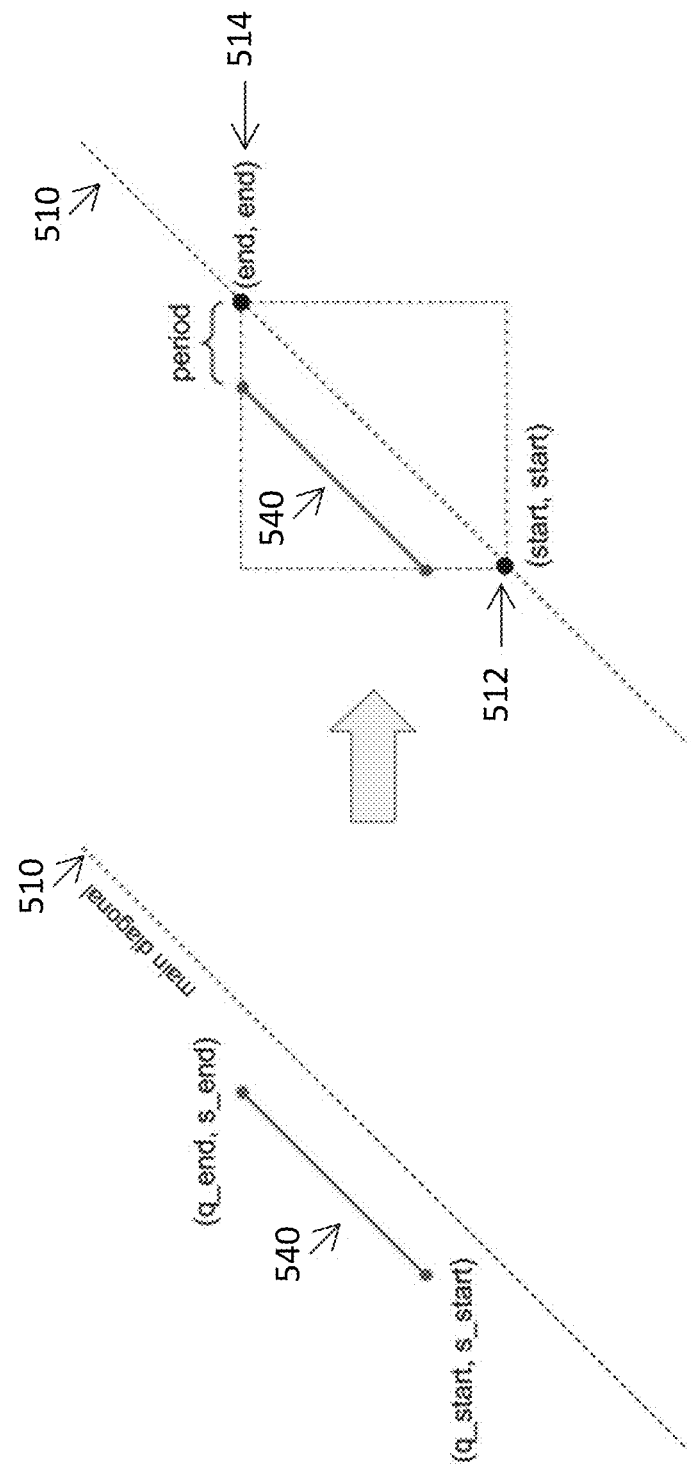

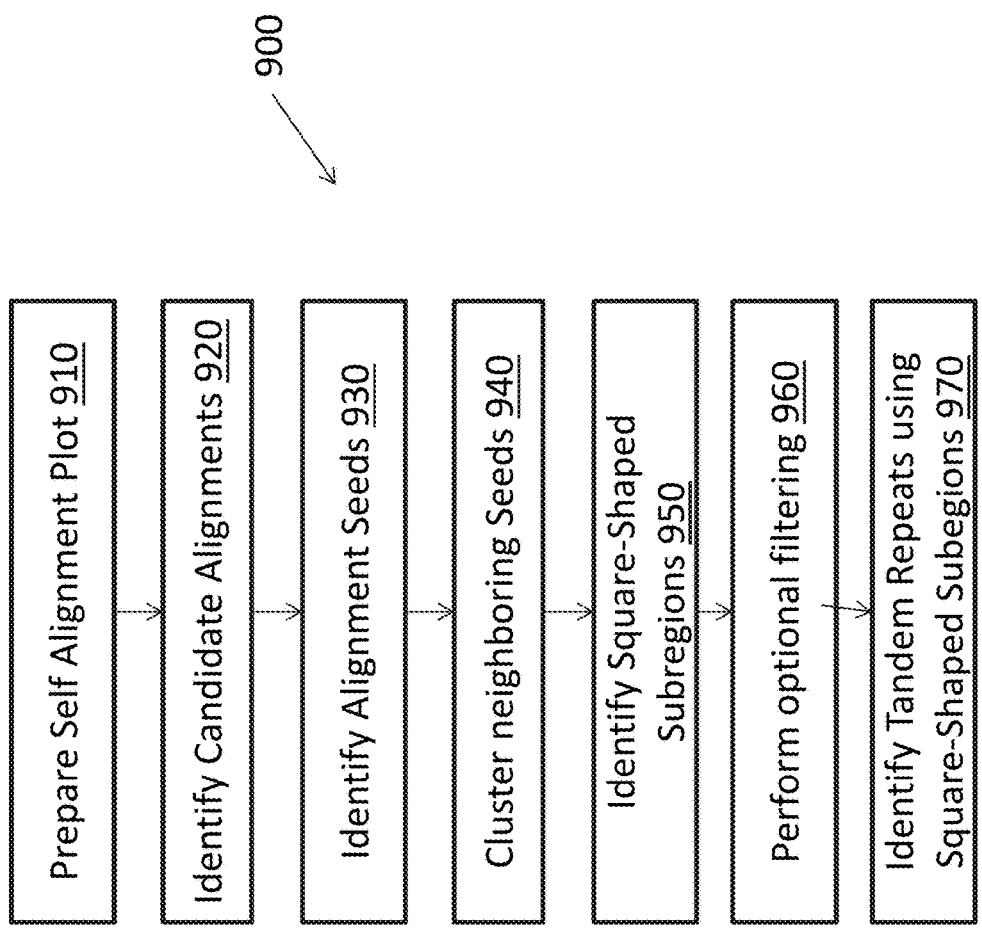

```
output:
10    134178250    134178346 period=26.0    repeat_number=3.7307692307
      identity=0.8210547368427              relative_coordinates=(17,113)

10    134178236    134178323 period=42.0    repeat_number=2.0952380952
      identity=0.6957                       relative_coordinates=(3,90)

10    134178234    134178303 period=36.0    repeat_number=1.9444444444
      identity=0.9412                       relative_coordinates=(1,70)

10    134178242    134178297 period=30.0    repeat_number=1.8666666667
      identity=0.7308                       relative_coordinates=(9,64)
```

FIG. 11

METHOD AND APPARATUS FOR IDENTIFYING TANDEM REPEATS IN A NUCLEOTIDE SEQUENCE

TECHNICAL FIELD

The present disclosure relates to identifying repeated subsequences (i.e., tandem repeats) that may be present in a longer nucleotide sequence.

BACKGROUND

Genomic mutational events can cause populations of individuals to exhibit large degrees of genetic variability. Tandem duplication is an example of a genomic mutational event, in which a short sequence of DNA is duplicated and inserted into the genome.

Subsequent duplication events result in a genomic sequence having a repeated pattern of one or more nucleotides, in which the repetitions are adjacent to one another. Such tandem repeats can span from simple, short sequences (e.g., a dinucleotide repeat "ATATAT" or trinucleotide repeat "CAGCAGCAG"), to more complex repetitive sequences with patterns spanning from tens to hundreds of nucleotides. Over time, individual copies within a tandem repeat may undergo additional mutation, resulting in the presence of approximate copies. Tandem repeats have been estimated to occur frequently (e.g., up to 10%) in genomic sequences.

Tandem repeats have been shown to cause human diseases and may play a variety of regulatory and evolutionary roles. Once characterized, they can also be important laboratory and analytical tools. For example, trinucleotide repeats are associated with a variety of diseases, such as fragile-X mental retardation, Huntington's disease, and myotonic dystrophy. Each of these diseases can result from a dramatic increase in copy number of a trinucleotide sequence from the normal range (e.g., tens of copies) to hundreds or thousands. Tandem repeats may also alter the structure of a DNA molecule, altering transcription and translation and ultimately affecting gene expression. Further, tandem repeats are often polymorphic across a population, and thus provide a valuable tool for linkage analysis, DNA fingerprinting, and genealogical DNA testing. Identifying and annotating reference genomes with tandem repeats is also important for next-generation sequencing alignments, in which many short sequence reads are mapped to a reference genome. An aligner that understands which portions of the genome include tandem repeats will be able to better map sequence reads to those regions. Further, regions of the genome having tandem repeats are often misassembled, which provides a useful clue to an aligner or variant caller. Thus, finding, annotating, and characterizing tandem repeats is an important tool.

Despite their simple nature, the detection and accurate characterization of tandem repeats can be a challenging problem. Existing tandem repeat detection techniques, such as Tandem Repeats Finder (TRF) can identify tandem repeats in a given nucleotide sequence by looking for runs of k-mer matches. Such k-mer matches can be found by sliding a window of length k along a nucleotide sequence and noting positions at which identical k-mers occur. Using TRF, whenever a new position is added to a list, an earlier occurrence of the k-mer is identified and the distance between the two sequences is calculated. This distance can be a possible pattern size for a tandem repeat. Distances can be compared to statistical criteria to generate a set of candidate tandem repeats and each candidate can be selected and aligned with the surrounding sequence in the genome to determine whether at least two copies of the pattern align. If an alignment is observed, a tandem repeat is reported. Although TRF does not require having prior knowledge of the pattern or the size of the repeat (i.e., k), it is computationally intensive and may require an excessive amount of processing time for large genomes. Further, TRF does not appear to be able to identify certain challenging tandem repeats that have longer pattern lengths and/or include excessive variations. For example, TRF appears to be unable to identify tandem repeats that are longer than 2000 base pairs.

SUMMARY

The present disclosure relates to identification of tandem repeats in a nucleotide chain.

In one aspect, a method of detecting a tandem repeat in a nucleotide sequence is featured. The method includes constructing a self-alignment plot of a nucleotide sequence and identifying one or more lines present in a self-alignment plot wherein such identified lines are positioned parallel to a central diagonal line of the self-alignment plot. (The central diagonal line indicates alignment of the nucleotide sequence with itself in the self-alignment plot.) The featured method also includes identifying a square-shaped subregion (SSS) containing at least one of the identified one or more lines and reporting presence of the tandem repeat in a region of the nucleotide sequence corresponding to the identified SSS.

In another aspect, the featured method includes acquiring information relating to a nucleotide sequence from a storage medium configured to store digital information and identifying one or more lines present in a self-alignment plot of the nucleotide sequence. The featured method may also include presenting (e.g., visualizing) the self-alignment plot to a human operator, receiving from the operator input for use in identifying a SSS containing at least one of the identified one or more lines, and reporting presence of the tandem repeat in a region of the nucleotide sequence corresponding to the identified SSS.

In other examples, any of the above aspects, or any system, method, apparatus, and computer program product method described herein, can include one or more of the described features.

Once one or more regions of the nucleotide sequence in which the tandem repeats are present are identified, the nucleotide sequence can be annotated based on the identified regions, and be displayed and/or presented to further processing.

An SSS can be identified such that a central diagonal line of the identified SSS lies along the central diagonal line which corresponds to the self-alignment. An SSS can be identified by one or more lines (sometimes referred to as "candidate alignments") contained in the identified SSS, such lines being located off of the diagonal. Each off-diagonal line can be identified by a start point and an end point, the start point and the end point being positioned along adjacent sides of the individual squares.

Each individual square, in turn, can be identified using a corresponding defining point which can be positioned at a corner of the square. The information relating to the choice of the specific seed and/or defining point can be received from the human operator or can be pre-determined.

The method further includes selecting one or more seed alignments within one or more of the identified SSS, each seed alignment having a start point and an end point, the start point and the end point being positioned along adjacent sides of individual squares. Two or more defining points obtained from neighboring or overlapping squares can be clustered to define a final alignment corresponding to the thus-identified tandem repeat.

In certain embodiments, the method of the invention includes:
a) constructing a self-alignment plot of a nucleotide sequence; identifying one or more candidate alignments present in the self-alignment plot, the identified candidate alignments being represented by lines positioned parallel to a central diagonal line of the self-alignment plot, the central diagonal line indicating alignment of the nucleotide sequence with itself;
b) identifying one or more square-shaped subregions (SSS) representing a tandem repeat and each associated with a plurality of identified candidate alignments by:
  i) estimating, for a plurality of the one or more candidate alignments, a defining point of an individual square, each candidate alignment having a start point and an end point, the start point and the end point being positioned along adjacent sides of the individual square;
  ii) selecting one or more seed alignments from the one or more candidate alignments;
  iii) associating the one or more candidate alignments with the one or more seed alignments, the associating comprising clustering defining points of individual squares of the one or more candidate alignments around the defining points of the one or more seed alignments, thereby determining a final SSS representing a tandem repeat; and
c) reporting presence of the tandem repeat in a region of the nucleotide sequence corresponding to the identified final SSS.

Determining the final alignment representing a final tandem repeat may include estimating the tandem repeats start, end, period, and identity for each cluster. The process of detecting a tandem repeat can also include filtering. For example, following clustering, two or more overlapping squares can be filtered such that squares having a lower quality than other identified squares are eliminated from further processing.

It should be appreciated that the present technology can be implemented and utilized in numerous ways, including without limitation as a process, an apparatus, a system, a device, a method for applications now known and later developed or a computer readable medium. In one aspect, the invention provides machine-readable non-transitory medium having stored thereon a computer program for performing the method of the invention.

Other aspects and advantages of the invention can become apparent from the following drawings and description, all of which illustrate the principles of the invention, by way of example only.

BRIEF DESCRIPTION OF THE DRAWINGS

The advantages of the invention described above, together with further advantages, may be better understood by referring to the following description taken in conjunction with the accompanying drawings. The drawings are not necessarily to scale, emphasis instead generally being placed upon illustrating the principles of the invention.

FIG. 1B illustrates another example of a tandem repeat located in chromosome 1 of the published human genome.

FIG. 5A illustrates an example of a candidate alignment that can be used for selecting a seed.

FIG. 5B illustrates another example of a candidate alignment that can be used for selecting a seed.

FIG. 9 illustrates a simplified flow diagram of the procedures that can be used by embodiments disclosed herein for identifying tandem repeats.

FIG. 11 provides an illustrative example of output produced by the method described herein.

DESCRIPTION

Embodiments described herein relate to detection of tandem repeats in nucleotide sequences through the use of discernable squares present in a self-alignment plot of a nucleotide sequence, where the confirmed presence and position of such a square is used as an indicator of the presence of a periodic region of the genome.

The present disclosure provides methods for detecting tandem repeats in a nucleotide chain. In certain embodiments, a method of detecting a tandem repeat in a nucleotide sequence is provided. The method comprises:
  constructing a self-alignment plot of a nucleotide sequence;
  identifying one or more square-shaped subregions (SSS) representing a tandem repeat and each associated with a plurality of identified candidate alignments by:
    i) estimating, for a plurality of the one or more candidate alignments, a defining point of an individual square, each candidate alignment having a start point and an end point, the start point and the end point being positioned along adjacent sides of the individual square;
    ii) selecting one or more seed alignments from the one or more candidate alignments;
    iii) associating the one or more candidate alignments with the one or more seed alignments, the associating comprising clustering defining points of individual squares of the one or more candidate alignments around the defining points of the one or more seed alignments, thereby determining a final SSS representing a tandem repeat; and reporting presence of the tandem repeat in a region of the nucleotide sequence corresponding to the identified final SSS.

Figure 1A:
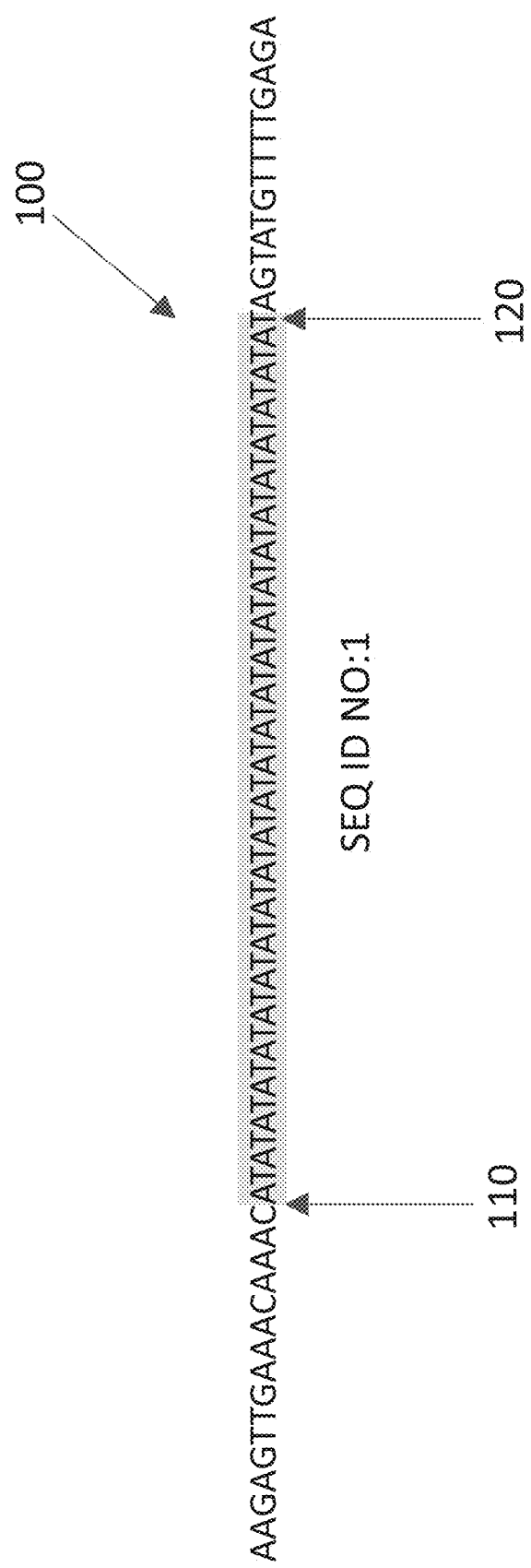
FIG. 1A illustrates an example of a tandem repeat located in chromosome 1 of the published human genome.

FIG. 1A illustrates an example of a tandem repeat located in chromosome 1 of the published human genome 100. Specifically, human genome (hg19), chromosome (chr1): hg19: chr1:177,572,128-177,572,208 is shown. As shown in FIG. 1A, the example nucleotide sequence includes a tandem repeat, which is a di-nucleotide repeat of the sequence "AT." The example tandem repeat ("AT") includes 100% identity with a period of 2 (i.e., the length of the repeated sequence or its period is 2 and the same sequence "AT" is identically repeated), a total length of 50, and a repeat number of 25 (i.e., the sequence is repeated 25 times). Further, as shown in FIG. 1A, the repeat sequence can have a starting point 110 and an ending point 120. The starting point 110 can mark the point in the nucleotide sequence where the tandem repeats begin to appear and the end point 120 can mark the point in the nucleotide sequence where the last observed tandem repeat ends.

FIG. 1B illustrates another example of a tandem repeat located in chromosome 1 of the published human genome 150. Specifically, human genome (hr19), chromosome (chr1): hg19: chr1:159,565,312-159,565,340 is shown. The example nucleotide sequence includes a number of tandem repeats (e.g., sequence: CACTAAGTG), however the repeated sequences are not 100% identical. Specifically, the sequence 150 contains two exact copies 151, 152 of "CACTAAGTG" and one imperfect copy "CACTCTGTG" 153. Generally, not every tandem repeat is necessarily perfect. If consecutive periods differ, for example, by a few base pairs, they can still be classified as repeats, though they are imperfect repeats. Generally, the differences existing in the various repeats can be characterized based on the identity of the region. For example, in the example shown in FIG. 1B, the difference between the third sequence 153 and the first 151 and second 152 sequences is 0.9. As such, the sequence shown in FIG. 1B can be said to have 90% identity. Presumably, the tandem repeat sequence 153 may have experienced additional mutation after the copied sequence was inserted into the genome.

Figure 2:
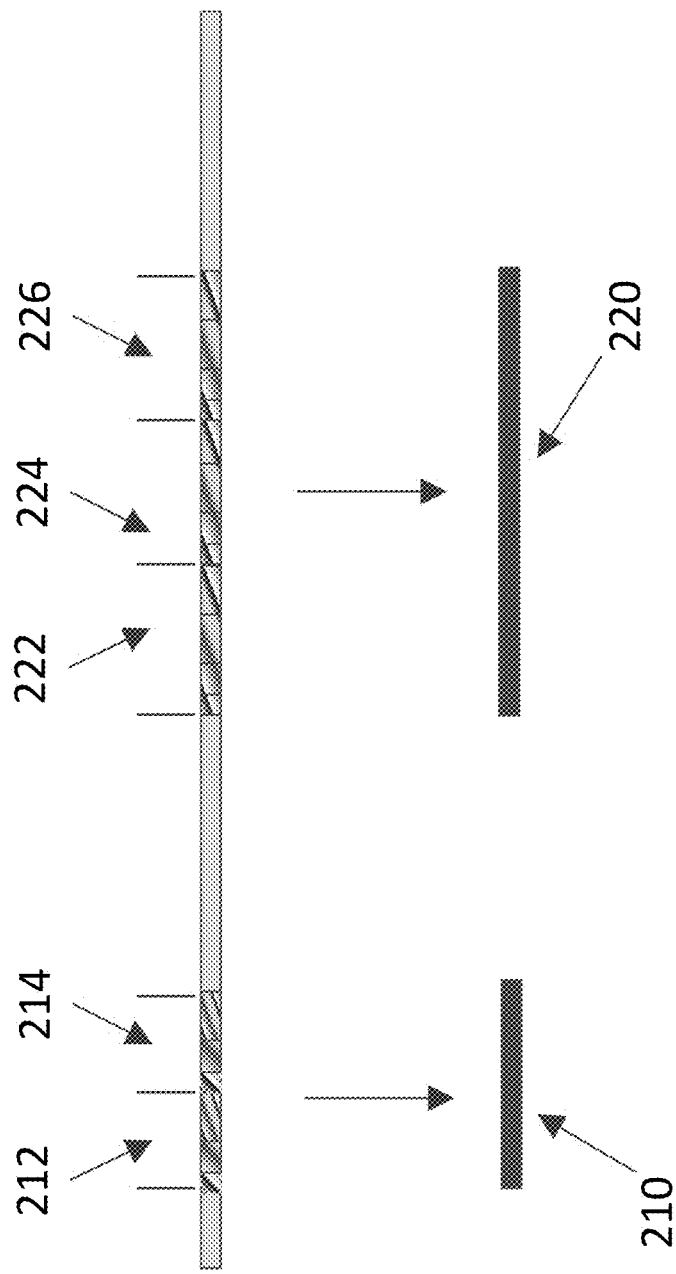
FIG. 2 is a simplified representation of a nucleotide sequence that includes a number of subsequences, each including two or more repeated sequences.

FIG. 2 is a simplified representation of a nucleotide sequence 200 that includes a number of subsequences 210, 220, each including two or more repeated sequences (i.e., tandem repeats). For example, the first subsequence 210, includes two tandem repeats 212, 214 and the second subsequence 220 includes three tandem repeats 222, 224, 226.

Figure 3:
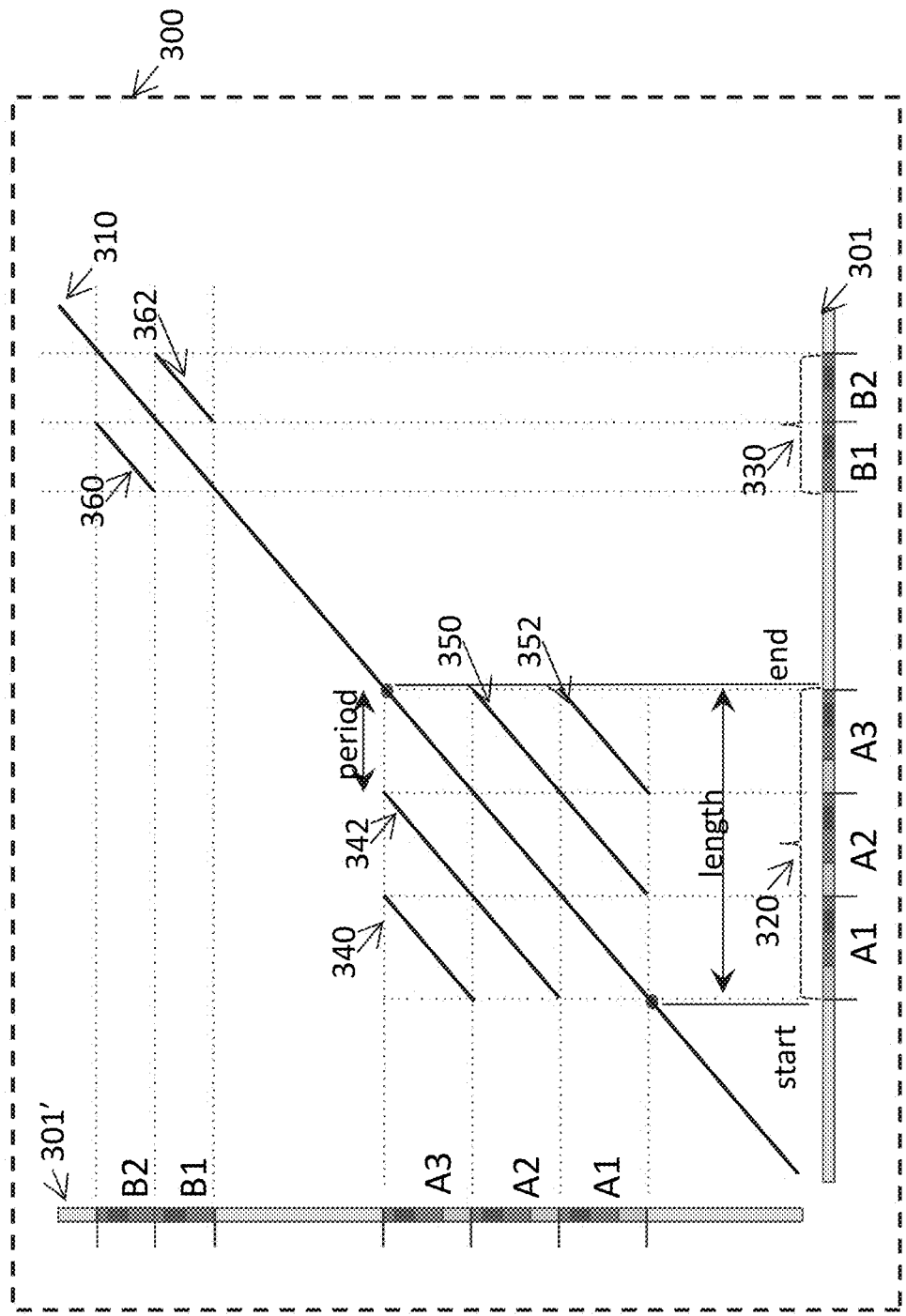
FIG. 3 is an example of a self-alignment plot that can be used by embodiments disclosed herein to identify tandem repeats in a nucleotide sequence.

FIG. 3 is an example of a self-alignment plot 300 that can be used by embodiments disclosed herein to identify tandem repeats in a nucleotide sequence. In this example, a nucleotide sequence 301 having two subsequences 320, 330 is shown. The first subsequence 320 includes three tandem repeats A1, A2, and A3 and the second subsequence 330 includes two tandem repeats B1 and B2. In the self-alignment plot 300, the same nucleotide sequence 301 is aligned against itself 301' to generate a plurality of candidate alignments.

The plot 300 can be a dot plot or any other visualization scheme known in the art. For example, a chart or "dot plot," in which the nucleotide sequence is represented on both the horizontal (X) and vertical (Y) axes can be used. Any (X,Y) coordinates in which the nucleotide sequence is identical can be marked with a dot. For example, as shown in FIG. 3, self-aligning the nucleotide sequence with itself can result in generation of an unbroken sequence of dots (i.e., a line 310) running diagonally across the plot; this represents an alignment of the sequence to itself This line can generally be the main diagonal line 310 of the plot 300. Repetitive sequences 320, 330 (i.e., regions in the genome which match well to one another) are represented as an unbroken sequence of dots (e.g., 340, 342, 350, 352, 360, 362) off of the main diagonal, but also travelling diagonally across the plot. In repetitive regions of the genome (e.g., A1, A2, A3, B1, B2), these unbroken sequences (e.g., 340, 342, 350, 352, 360, 362) form visible squares, revealing the presence of tandem repeats. Further, as shown in FIG. 3, these unbroken sequences can be used to determine various characteristic features of the tandem repeats, such as the length of the subsequence including the tandem repeats, the repetition period, and the location within the nucleotide chain where the tandem repeat starts and ends.

Figures 4A, 4B:
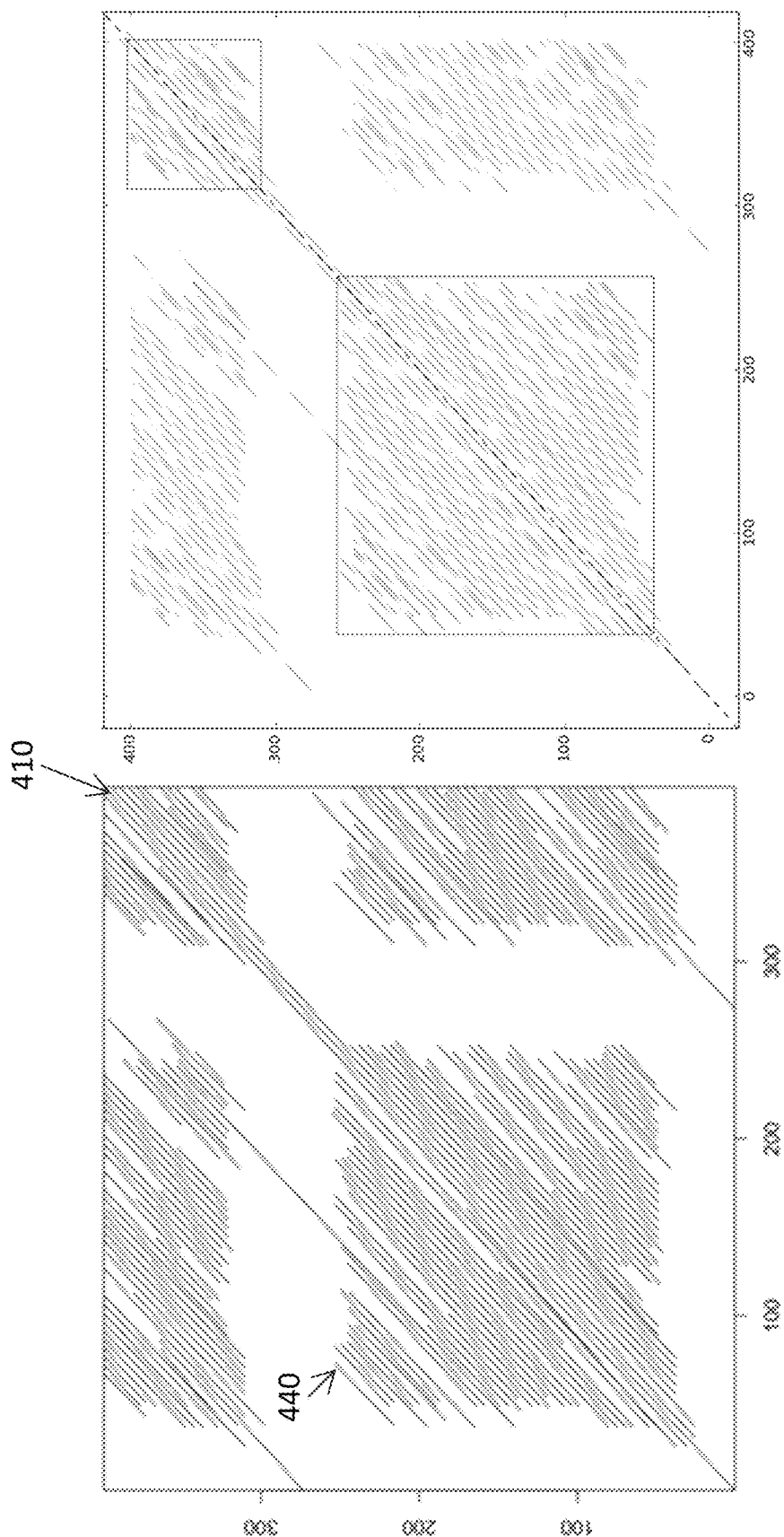
FIG. 4A illustrates an example of a self-alignment plot obtained by self-aligning a nucleotide sequence against itself.
FIG. 4B illustrates an example of the candidate alignments that can be used by the embodiments described herein.

FIG. 4A illustrates an example of a self-alignment plot obtained by self-aligning a nucleotide sequence (specifically, chromosome 16, positions 33,900,385-33,900,784) against itself. As shown in FIG. 4A, the self-alignment plot includes an unbroken sequence of dots running diagonally across the plot (i.e., main diagonal 410) and a number of unbroken and partially unbroken lines (e.g., diagonal 440) that appear on either sides of the main diagonal 410. Self-alignment plots, such as the plot shown in FIG. 4A, are often inherently noisy. To accurately and quickly identify squares representing presence of the tandem repeats in the dot plot, candidate alignments can be generated from the self-alignment data. Candidate alignments off of the main diagonal can show the presence of squares that defines regions of the nucleotide sequence having tandem repeats.

The candidate alignments can be selected using various techniques. For example, candidate alignments can be selected by identifying locations in the dot plot, in which there are a number of nucleotide matches (in the Figures, shown as "dots") along a diagonal line. Some number of gaps or mismatches within each alignment, which correspond to gaps and upward or right shifts in a connected path, can be allowed. Techniques known in the art (e.g., BLAST® or the Smith-Waterman algorithm) can be used to identify alignments in the data.

FIG. 4B illustrates the self-alignment plot of FIG. 4A with sets of candidate alignments forming off of the main diagonal highlighted by visible squares. As shown in FIG. 4B, these stretches of unbroken lines off of the main diagonal can be identified as candidate alignments, or portions of the nucleotide sequence 301 that can align well to another portion of itself 301'. As noted above, the parameters of each candidate alignment can include two start positions (i.e., representing the bottom-left position of the alignment along the X and Y axes, corresponding to the start positions in the nucleotide sequence associated with the X axis and the nucleotide sequence associated with the Y axis), two end positions (for the top-right position), and a length between. The visible squares are positioned over the main diagonal line corresponding to the tandem repeat, and contain the candidate alignments that are associated with that repeat. The candidate alignments can be further refined to identify squares, and thus tandem repeats within the nucleotide sequence.

It should be noted that although typical image processing techniques may be able to help in identification of the squares that indicate the presence of tandem repeats, such image processing techniques often fail to identify the corresponding region accurately. Embodiments described herein overcome these difficulties by identifying particular candidate alignments that can be used for inferring the parameters of a square that defines a tandem repeat. These alignments are referred to as "seeds." A candidate alignment is identified as a seed based on an evaluation of the size of the repetitive region that it defines relative to the size of the alignment itself.

Specifically, an alignment is identified as a seed by identifying parameters of a square (i.e., the repetitive region) that would have produced the candidate alignment, based on the starting and ending positions of the candidate alignment. FIG. 5A and FIG. 5B illustrate an example of a candidate alignment (e.g., an off-diagonal line) 540 that can be used for selecting a seed. As shown in FIG. 5A and FIG. 5B, for a given candidate alignment 540 (off of the main diagonal 510), the inferred start 512 for the region can be the minimum of either starting position (e.g., those points shown as (q_start, s_start), corresponding to the nucleotide sequence associated with the X-axis and the nucleotide sequence associated with the Y-axis), the inferred end 514 can be the maximum of either ending position (e.g., points shown as (q_end, s_end)), and the inferred period can be the linear distance between the inferred end 514 and the ending position of the candidate alignment (e.g., the length shown as "period"). Similarly, the inferred period can be the distance between the inferred start 512 and the starting position of the candidate alignment.

It should be noted that each alignment typically has two starting points because both segments start somewhere in the reference sequence. Further, in candidate alignments having gaps (i.e., in which a portion of the candidate alignment shifts closer to or farther away from the main diagonal), the end position may be accounted for by including an offset value reflecting the number of gapped positions; alternately, one may simply use the actual end position without the offset value.

Figure 6B:
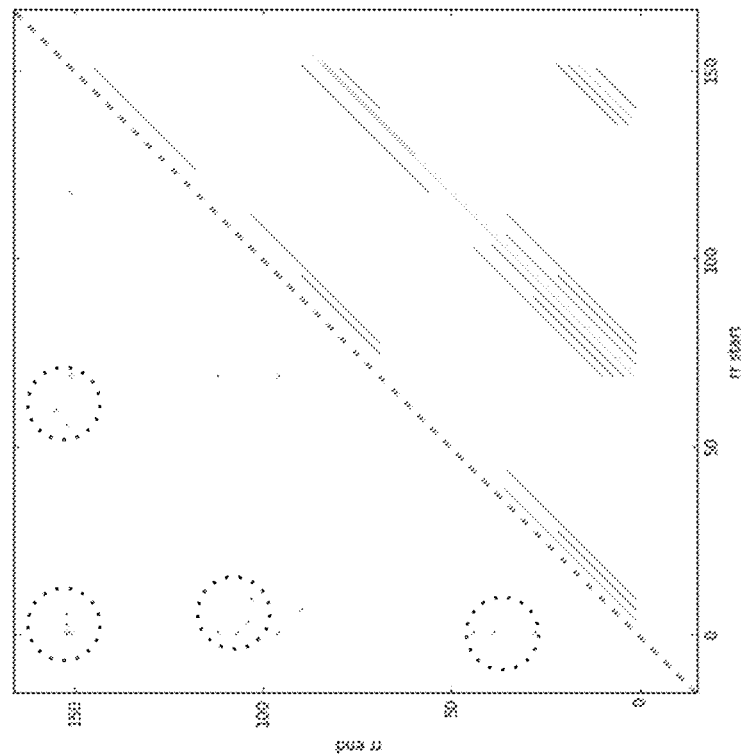
FIG. 6B illustrates an example of alignments clusters that can be obtained using defining points.
Figure 6A:
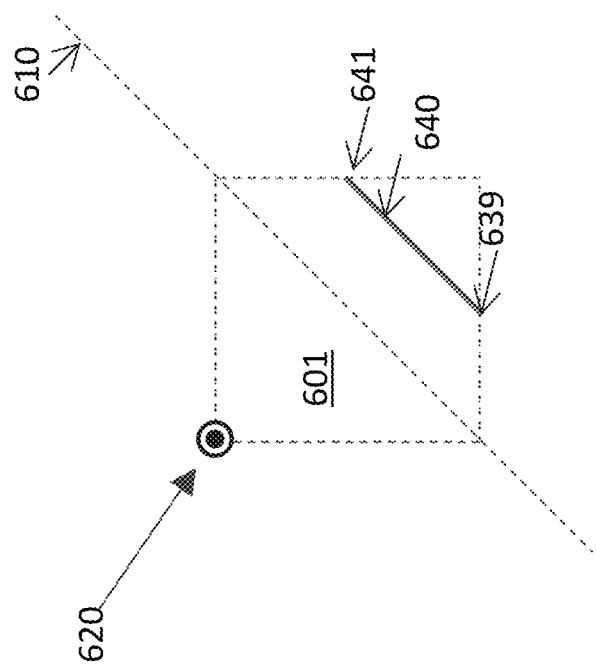
FIG. 6A illustrates another example of a candidate alignment that can be used for selecting a seed.

FIG. 6A illustrates another example of a candidate alignment 640 that can be used for selecting a seed. As shown in FIG. 6A, a candidate alignment can be used to identify a square that can contain the candidate alignment 640 as an off of the main diagonal 610 line. Specifically, as shown in FIG. 6A, the start 639 and end 641 points of the candidate alignment 640 can be used to find a point 620 that marks a corner of a square 601, whose main diagonal is along the main diagonal 610 and includes the start point 639 and end point 641 on its adjacent sides. Accordingly, each alignment 640 can represent a square or semi-square shaped region 601 uniquely represented by a defining point 620. The defining point 620 is a point positioned on one corner of the square or semi-square region 601 defined by the candidate alignment.

FIG. 6B is an example of alignments clusters that can be obtained using defining points 620. The candidate alignments can be clustered by various factors, such as the start and end points of their implied regions (e.g., square or semi-square regions defined by the clusters). As shown in FIG. 6B, the defining points 620 reflect the start points of their implied regions, i.e., the top-left corner of the square defined by that particular candidate alignment. Defining points close to one another likely represent candidate alignments that were generated from the same tandem repeat.

Once the squares and defining points for each candidate alignment have been estimated, the candidate alignments are evaluated to determine whether a given candidate alignment can be an optimal seed for clustering additional alignments to the estimated square. An optimal seed for clustering is usually a seed that is not too close to either the main diagonal or the upper-leftmost corner of the square. For example, an optimal seed can be selected using alignments having a length ranging from 25% to 75% of the length of a corresponding squared-shaped region (also referred to as squared-shaped subregion, SSS, or simply a "square"). Candidate alignments having a length ranging from 10% to 90% of the length of region are often sufficiently robust for selecting an optimal seed.

Additionally or alternatively, an optimal seed can be selected by choosing alignments that are longer than 0.75 times an estimated period for the tandem repeat (e.g., length of area labeled as "period" in FIG. 5B) and shorter than three times the estimated period. This approach of choosing alignments rejects pseudo-alignments (e.g., long alignments running close to the main diagonal) and filters out short, isolated alignments that are typically non-tandem repeats.

Further, once a set of optimal seed alignments have been identified, candidate alignments (and even other seed alignments) that are close to one another can be assumed to represent roughly the same square. Accordingly, alignments around an optimal seed can be clustered to represent a single square. Such clustering can reduce the total number of resulting squares to process and provide a smaller and more refined set for subsequent analysis.

Clustering can begin by estimating the start and end points of a region for every candidate alignment, and iterating through every seed. Clusters can be created by associating the candidate alignments that have start and end points within a given radius of the seed alignment start and end points. For example, in some embodiments, candidates within 5%, 10%, or 25% radius of the length of the seed can be used. Further, seed alignments can be used to cluster other alignments together. The clusters can in turn be used to improve the estimated dimensions of the square or semi-square region resulting from presence of repetitive regions in a reference nucleotide sequence.

In some embodiments, certain seed alignments can become associated with other seeds during clustering and be removed from the pool of un-clustered seeds. In such embodiments, the result of clustering can depend on the seed processing order. The processing order can be defined based on the distance from the main diagonal (e.g., starting close and then moving away), which can work well for the overall clustering. In particular, processing seed alignments in an order moving away from the main diagonal is preferable because it improves the likelihood of correctly identifying short tandem repeats (which exhibit relatively smaller square-shaped subregions). Near the main diagonal, many of the seed alignments represent the same short tandem repeat and are close to one another. By starting processing from the main diagonal, these seed alignments are properly clustered together, without potentially disturbing seed alignments from clusters that are far from the main diagonal (i.e., those clusters representing longer tandem repeats with correspondingly larger square-shaped subregions). In contrast, processing seeds by starting away from the main diagonal and moving inwards has the potential to incorrectly associate seed alignments from a shorter tandem repeat with a larger one.

Once clustering is complete, the candidate alignments clustered around each seed can be used to generate a more accurate estimate of the parameters of a square that is defined by the cluster of candidate alignments. For example, the start of a given square can be the median of start points of its candidate alignments and the end can be the median of the end points of its candidate alignments. The period of repetition for each tandem repeat can be determined based on the median of the nearest neighbor distances between consecutive alignments counting from the main diagonal. The identity among the tandem repeats can be measured based on the weighted average of the identities. Various other measures could also be used to generate an improved estimate of the parameters of a square based on the properties of its clustered candidate alignments and their associated squares.

Figure 7:
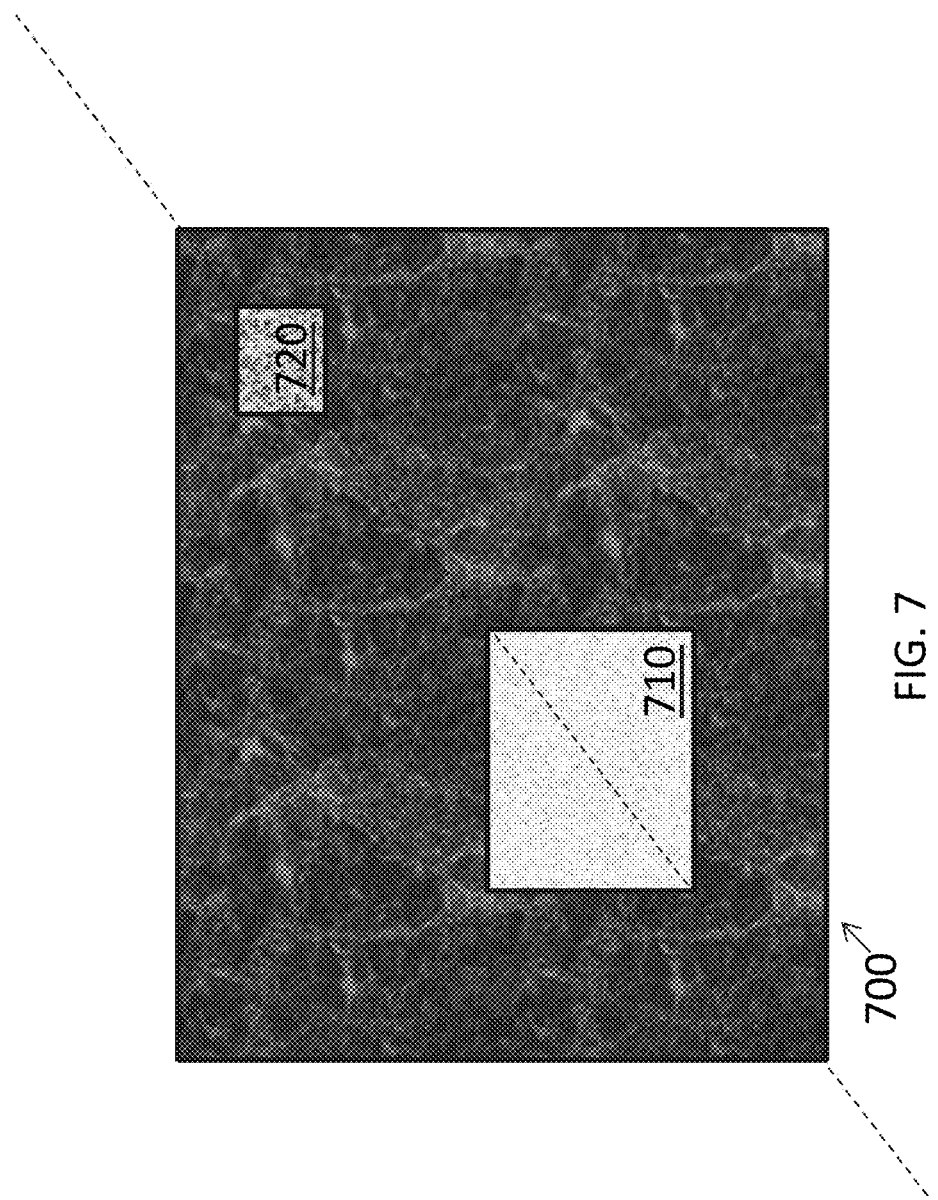
FIG. 7 illustrates an example of overlapping tandem repeat regions that can be identified using the embodiments described herein.

Clustering can result in a large set of squares defining regions of tandem repeats. However, these regions can include low quality or overlapping regions. FIG. 7 illustrates an example of overlapping tandem repeat regions that can be identified using the embodiments described herein. As shown in FIG. 7, a strongly pronounced square region 700 may be identified as including one or more strongly pronounced smaller regions 720 and/or one or more less plausible regions 710.

Various filtering techniques can be used to improve the quality of the regions and/or remove any overlapping regions. For example, regions having certain characteristics (e.g., shorter regions, overlapping regions, regions having larger periods than other regions, regions having smaller identity than others, etc.) can be removed. Removal/filtering of such regions can prevent reporting of less plausible regions (e.g., regions with longer periods) that may reside within more strongly pronounced regions. Similarly, squares that are completely located within other squares and have significantly lower quality levels than their surrounding squares may be removed. Accordingly, in some embodiments filtering includes eliminating individual squares based on a lower quality/identity than other identified squares, for example, squares of lower quality within a higher quality square are eliminated. Filtering individual squares may also be based on quality/identity below a defined threshold. In certain embodiments, quality may also be indicative of the number of candidate alignments associated with a region. For example, a region having few associated candidate alignments may be filtered.

Figure 8B:
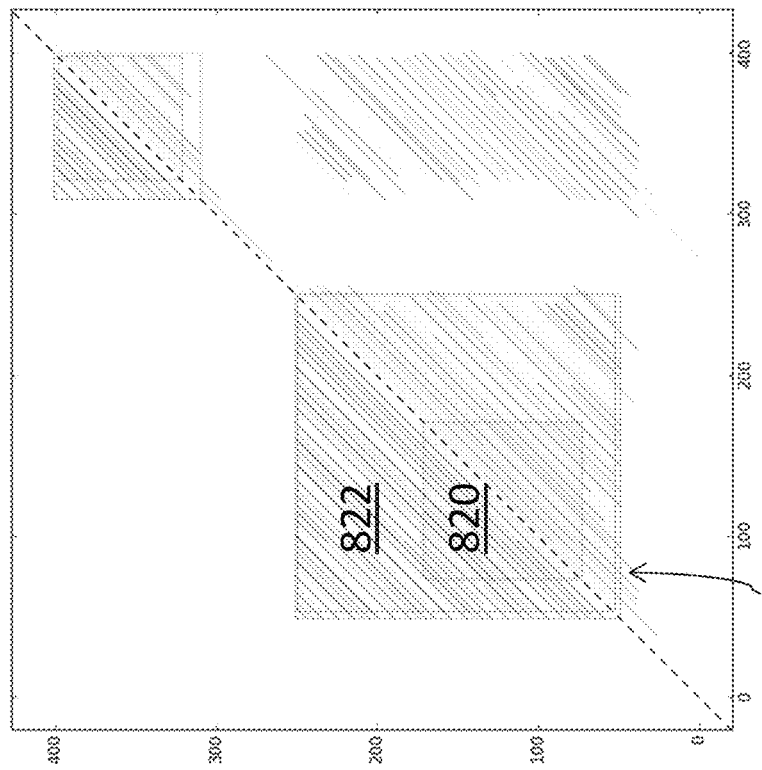
FIG. 8B illustrates an example of overlapping squares that can be identified using the embodiments described herein.
Figure 8A:
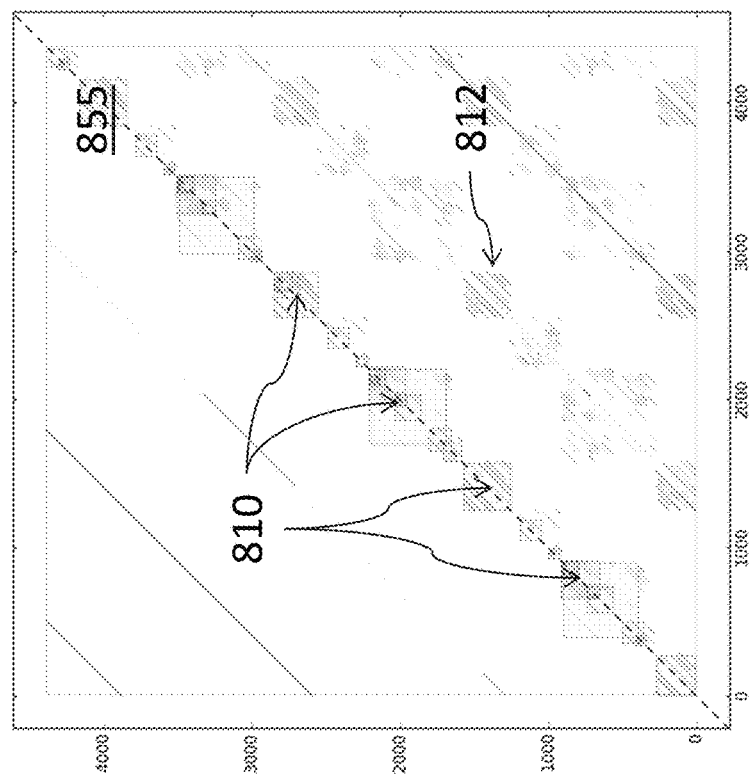
FIG. 8A illustrates the identification results obtained from analyzing nucleotide data.

FIG. 8A illustrates the identification results obtained from analyzing the nucleotide data obtained from a nucleotide sequence from the GRCh37 human genome, chromosome 7, from positions 56,438,076-56,442,464. As shown in FIG. 8A, squares having a uniform density 810 can be obtained using the candidate alignments. However, overlapping squares 820, 822, 824 (FIG. 8B) can exist. FIG. 8B illustrates an example of such overlapping squares 820, 822, 824. As shown, one square 824 can be slightly larger than another square 822. Such incidences of nearly similarly sized and positioned squares can indicate the presence of a tandem repeat that extends further than other tandem repeats and possibly has sequences of lower identity or quality. For example, square 820 is of high quality, and is nearly entirely filled with candidate alignments (as evidenced by the number of full-line candidate alignments within the square on the lower-right side of the main diagonal). In contrast, square 822 is of lesser quality and includes many alignments which do not extend the full length of the diagonal between the lower and right edges of the square. Finally, square 824 is only slightly larger than square 822, and likely indicates an additional low-quality repeat located at the 5' end of the tandem repeat identified by square 822. Quality can refer to various measures of the estimated parameters of the square and/or tandem repeat, such as identity.

The results obtained can be subsequently scored and analyzed. For example, the results obtained can be subsequently evaluated to provide a score for each tandem repeat using various characteristics of the tandem repeat, such as its entropy and variance.

Embodiments described herein, when applied to the first chromosome of the human genome (chr1 hg19), and after filtering of any regions having an identity less than 75%, appear to find tandem repeats that are not presently identifiable by existing techniques. Specifically, embodiments described herein, in one experiment, were able to find 2,142 tandem repeats that were not found by the Tandem Repeat Finder Database. However, the Tandem Repeat finder could find 3,686 repeats that were not found by the present embodiments. An analysis of the results seems to indicate that the present embodiments can find longer regions, with longer repetition periods, and lower identity, than those identified by the Tandem Repeat Finder Database. For example, we find that many of the new regions identified have periods of 10-100, and lengths of 30-200, with an average repeat number of 2. In various embodiments, the nucleotide sequence can be a whole genome sequence or portion of a genome, a sequence of a chromosome or portion of a chromosome, or a sequence read of, for example, 100-100,000 bp.

FIG. 8A also illustrates the presence of visible squares off of the main diagonal line (e.g., a set of alignments 812). It should be noted that there are many alignments off of the main diagonal that do not represent a square bisected by the main diagonal. These regions represent random alignments in the genome that can represent non-tandem repeats, segmental duplications, and other repetitive regions in the genome. Methods of the disclosure can minimize processing time by effectively ignoring these alignments by selecting appropriate seed alignments. For example, each of the alignments in the set of alignments 812 would result in a relatively large square corresponding to the main diagonal. Each of these alignments are relatively short compared to the region defined by their inferred squares on the main diagonal, and thus would not be selected as seeds for clustering.

However, in certain examples, these regions may represent tandem repeats that are duplicated in different sections of the genome, and thus could be analyzed or inferred from the presence or identification of tandem repeats along the main diagonal (e.g., by comparing identified tandem repeats to one another.) For example, the set of alignments 812 are likely a result of two of the tandem repeats represented by the squares 810. Although not discussed herein, these regions can be analyzed to discover other repetitive regions in the genome. For example, one could attempt to cluster the set of alignments 812 around a separate diagonal line, perhaps inferred from the set of alignments 812 themselves.

FIG. 9 illustrates a simplified flow diagram of the procedures 900 that can be used by embodiments disclosed herein for identifying tandem repeats. As noted previously, a self-alignment plot can be prepared 910 and used by embodiments disclosed herein to identify tandem repeats in a nucleotide sequence. The self-alignment plot can be a dot plot or any other visualization scheme known in the art. For example, a chart or "dot plot," in which the nucleotide sequence is represented on both the horizontal (X) and vertical (Y) axes can be used. Any (X,Y) coordinates in which the nucleotide sequence is identical can be marked with a dot or any other identifier on the self-alignment plot.

The nucleotide sequence used to generate the self-alignment plot can be any nucleotide sequence. For example, the nucleotide sequence could be a previously existing reference genome. Alternately, the nucleotide sequence could be a sequence read or a set of sequence reads generated using next-generation sequencing technologies, such as by an Illumina® MiSeq desktop sequencer or a Pacific Biosciences® sequencer using Single Molecule, Real-Time (SMRT) sequencing technology. MiSeq sequence reads can span from 50-300 bp, whereas the SMRT sequencing can generate read lengths of up to 60,000 bp. Because methods according to the disclosure are uniquely able to process longer nucleotide sequences compared to TRF, they can be particularly useful for annotating long sequence reads. Further, in certain embodiments, methods according to the present disclosure may also be used to identify tandem repeats within protein sequence data.

Self-aligning of the nucleotide sequence with itself can result in generation of an unbroken sequence of dots (such as line 310, shown in FIG. 3) that runs diagonally across the plot and represents an alignment of the sequence to itself. Repetitive sequences are also presented on the self-alignment plot as unbroken or partially unbroken lines or sequences of dots (or other markers). These unbroken sequences represent various characteristic features of the tandem repeats, such as the length of the subsequence including the tandem repeats, the repetition period, and the location within the nucleotide chain where the tandem repeat starts and ends.

Candidate alignments can be identified from the self-alignment data 920 using various techniques. For example, candidate alignments can be selected by identifying locations in the dot plot, in which there are a number of nucleotide matches (in the Figures, shown as "dots") along a diagonal line. As noted above, some number of gaps or mismatches within each alignment may be allowed. Techniques known in the art (e.g., BLAST® or the Smith-Waterman algorithm) can be used to identify alignments in the data.

The identified candidate alignments can be further refined to identify tandem repeats 930. Specifically, candidate alignments that can be used for inferring the parameters of a square that defines a tandem repeat can be identified. These candidate alignments or "seeds" are identified based on an evaluation of the size of the repetitive region that it defines relative to the size of the alignment itself.

Once candidate alignments designated as seeds are identified, candidate alignments that are close to one another are assumed to represent roughly the same square (i.e., they are assumed to have been generated from the same tandem repeat) and are clustered together to represent a single square 940. Such clustering can reduce the total number of resulting squares to consider and provide a smaller and more refined set for subsequent analysis. Square shaped regions corresponding to the clustered seeds are then identified 950. An optional filtering procedure 960 can also be applied to remove squares or regions having certain characteristics (e.g., shorter regions, overlapping regions, regions having larger periods than other regions, regions having smaller identity than others, etc.). The presence of tandem repeats in the nucleotide chain and various characteristics of the tandem repeat (e.g., length, period, etc.) can be determined 970 using the identified square-shaped regions.

Once a tandem repeat has been determined 970, the nucleotide sequence may then be annotated with this information. In the case of a reference genome, this information may be indicative of a portion of the genome that may be poorly assembled (as repetitive regions are notoriously hard to assemble). In a next-generation sequencing alignment, performing a de novo assembly in this region may help improve variant calling. Similarly, annotating a sequence read with this information can help improve downstream tasks, such as reference alignment and de novo assembly.

Figure 10:
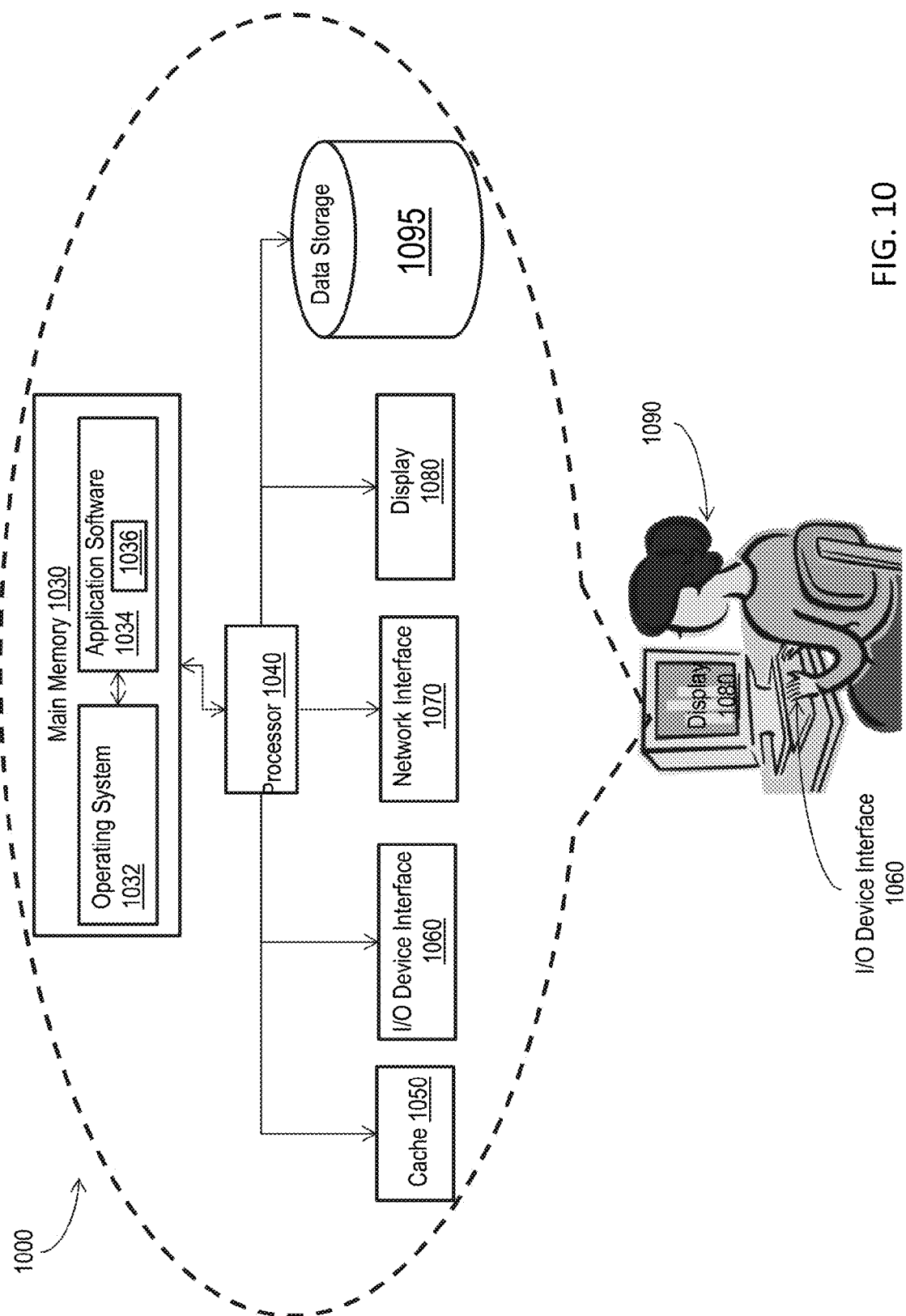
FIG. 10 is an example illustration of digital electronic circuitry or computer hardware that can be used with the embodiments disclosed herein.

FIG. 10 is an example illustration of digital electronic circuitry or computer hardware 1000 that can be used with the embodiments disclosed herein. The techniques described herein, without limitation, can be implemented in digital electronic circuitry or in computer hardware that executes software, firmware, or combinations thereof The implementation can be as a computer program product, for example a computer program tangibly embodied in a machine-readable storage device, for execution by, or to control the operation of, data processing apparatus, for example a computer, a programmable processor, or multiple computers.

The program codes that can be used with the embodiments disclosed herein, for example the program codes associated with an application 1036 that employs procedures similar to those described in FIG. 9, can be implemented and written in any form of programming language, including compiled or interpreted languages, and be deployed in any form, including as a stand-alone program or as a component, subroutine, module, or other unit suitable for use in a computing environment. A computer program can be implemented on or be executed on one computer or on multiple computers at one site or distributed across multiple sites and interconnected by a communications network.

One or more programmable processors can execute a computer program to operate on input data, perform function and method steps described herein, and/or generate output data. An apparatus can be implemented as and/or methods described herein can be performed by special purpose logic circuitry, such as a field programmable gate array (FPGA) or an application specific integrated circuit (ASIC). Further, computer programs and/or the processor/special circuitry can be used to implements the embodiments described herein.

The digital circuitry 1000 can include a main memory unit 1030. The main memory 1030 can include an operating system 1032 and be configured to implement various conventional operating system functions. For example, the operating system 1032 can be responsible for memory management, controlling access to various devices, and/or implementing various functions described herein. The main memory 1030 can also hold application software 1034 and be a read-only memory or a random access memory or both. For example, the main memory 1030 can include various application software, computer executable instructions, and data structures, including computer executable instructions and data structures that implement aspects of the embodiments described herein. Further, the main memory 1030 can be any form of non-volatile memory included in machine-readable storage devices suitable for embodying computer program instructions and data. For example, the memory 1030 can be one or more of a semiconductor memory device (e.g., EPROM or EEPROM), magnetic disk (e.g., internal or removable disks), magneto-optical disks, flash memory, CD-ROM, and/or DVD-ROM disks. Any suitable type of machine-readable non-transitory medium can be used for having stored thereon a computer program for performing the method of the invention and is provided herein.

The main memory 1030 can connect to a processor 1040. The processor 1040 and the main memory 1030 can be included in or supplemented by special purpose logic circuitry. The processor 1040 can include a conventional central processing unit (CPU) comprising processing circuitry that can execute various instructions and manipulate data structures from the main memory 1030. For example, the processor 1040 can be a general and/or special purpose microprocessor and any one or more processors of any kind of digital computer. Generally, the processor 1040 can receive instructions and data from the main memory 1030 and executes the instructions. The instructions and other data can be generally stored in the main memory 1030.

The processor 1040 can be coupled to a cache 1050 that stores copies of the data from the most frequently used main memory 1030 locations. The processor 1040 can also be connected to various interfaces via an input/output (I/O) device interface 1060, one or more data storage devices 1090, a network interface 1070 that is responsible for providing the circuitry 1000 with a connection to a communications network (not shown), and a display 1080 for receiving and/or displaying information. The processor can be arranged to transfer data to or receive data from the storage device 1090. The storage device 1090 can store the data used by the embodiments described herein, for example the nucleotide data employed herein. A user 1090 can interact with the digital circuitry 1000 to input data and information into the digital circuitry for use by the embodiments described herein. In particular, a user may load an application executing methods of the present disclosure, configure the application (e.g., by setting parameters), input data, copy data from a remote network location, load the data into the application, execute the application, run an analysis within the application, collect results, view a visual representation of the results (e.g., as shown in the embodiments herein), save results to disk, and/or upload the results to a remote network location.

In some embodiments, the self-alignment plot can be presented to user 1090 (also referred to as a human operator). The output may also be visualized for use by a human operator, for example, the annotated nucleotide sequence can be displayed to the operator. The operator may also provide input information for use in identifying one or more SSS; receiving one or more parameters of seed alignments or one or more parameters for filtering and/or information on one or more defining points.

Exemplary results may include the chromosome, start position, end position, period, repeat number, identity, and relative coordinates of a tandem repeat within a larger nucleotide sequence. One example of output is provided in FIG. 11.

While the foregoing description has been directed to specific embodiments, it will be apparent, however, that other variations and modifications may be made to the described embodiments, with the attainment of some or all of their advantages. Accordingly, this description is to be taken only by way of example and not to otherwise limit the scope of the embodiments herein. Therefore, it is the object of the appended claims to cover all such variations and modifications as come within the true spirit and scope of the embodiments herein.

---

---

The invention claimed is:

1. A method of annotating a reference sequence with a tandem repeat, the method comprising using at least one computer hardware processor to perform:

constructing a self-alignment plot of the reference sequence, the self-alignment plot comprising a dot plot in which the reference sequence is represented on both the horizontal (X) and vertical (Y) axes, wherein any (X,Y) coordinates in which the reference sequence is identical are marked with a dot;

identifying one or more candidate alignments present in the self-alignment plot, the identified candidate alignments being represented by lines positioned parallel to a central diagonal line of the self-alignment plot, the central diagonal line indicating alignment of the reference sequence with itself;

identifying one or more square-shaped subregions (SSS) representing a tandem repeat and each associated with a plurality of identified candidate alignments by:

i) estimating, for a plurality of the one or more candidate alignments, a defining point of an individual square, each candidate alignment having a start point and an end point, the start point and the end point being positioned along adjacent sides of the individual square;

ii) selecting one or more seed alignments from the one or more candidate alignments;

iii) associating the one or more candidate alignments with the one or more seed alignments, the associating comprising clustering defining points of individual squares of the one or more candidate alignments around the defining points of the one or more seed alignments, thereby determining a final SSS representing a tandem repeat; and annotating the reference sequence with the presence of the tandem repeat in a region of the reference sequence corresponding to the identified final SSS.

2. The method of claim 1, wherein the defining point of the individual squares are positioned at a corner of the respective square.

3. The method of claim 1, further comprising filtering individual squares.

4. The method of claim 3, wherein filtering includes eliminating individual squares based on a lower quality than other identified squares.

5. The method of claim 4, wherein squares of lower quality within a higher quality square are eliminated.

6. The method of claim 3, wherein filtering individual squares is based on quality below a defined threshold.

7. The method of claim 1, wherein annotating the reference comprises storing the annotation in a database.

8. The method of claim 1, wherein the reference sequence is a whole genome sequence or portion of a genome, a sequence of a chromosome or portion of a chromosome, or a sequence read of 100-100,000 bp.

9. The method of claim 1, wherein the candidate alignments are pre-selected using an alignment algorithm chosen from BLAST® and the Smith-Waterman algorithms.

10. The method of claim 1, wherein the seed alignments are selected based on parameters of the square defined by the corresponding alignment.

11. The method of claim 1, wherein the seed alignments are selected based on having a length shorter than a predetermined length, and/or shorter than the length of a predetermined percentage of the putative tandem repeat region.

12. The method of claim 1, wherein the seed alignments are selected on the basis of their length being 25% to 75% of the putative tandem repeat region.

13. The method of claim 1, wherein the seed alignments are selected to be longer than 0.75 times an estimated period (the estimated period being determined from a square inferred from a seed alignment) and shorter than three times the estimated period.

14. The method of claim 1, further comprising presenting the self-alignment plot to a human operator.

15. The method of claim 1, wherein the reporting includes visualizing output for use by a human operator.

16. The method of claim 1, further comprising receiving from a human operator information for use in identifying one or more SSS; receiving one or more parameters of seed alignments or one or more parameters for filtering and/or information on one or more defining points.

17. The method of claim 1, further comprising presenting the annotated reference sequence to a human operator.

18. The method of claim 1, wherein the reporting includes identification of the specific nucleotides positions of the tandem repeat.

19. A machine-readable non-transitory medium having stored thereon a computer program for performing the method of claim 1.

20. The method of claim 1, further comprising aligning a plurality of sequence reads to the annotated reference sequence.

* * * * *

SEQUENCE LISTING

```
<160> NUMBER OF SEQ ID NOS: 2

<210> SEQ ID NO 1
<211> LENGTH: 80
<212> TYPE: DNA
<213> ORGANISM: Artificial Sequence
<220> FEATURE:
<223> OTHER INFORMATION: Illustrative sequence used in Figure 1A

<400> SEQUENCE: 1
aagagttgaa acaaacatat atatatatat atatatatat atatatatat atatatatat        60
atatatagta tgttttgaga                                                    80

<210> SEQ ID NO 2
<211> LENGTH: 27
<212> TYPE: DNA
<213> ORGANISM: Artificial Sequence
<220> FEATURE:
<223> OTHER INFORMATION: Illustrative sequence used in Figure 1B

<400> SEQUENCE: 2
cactaagtgc actaagtgca ctctgtg                                            27
```